(12) United States Patent
Schütte et al.

(10) Patent No.: US 7,332,139 B2
(45) Date of Patent: Feb. 19, 2008

(54) PROCESS AND DEVICE FOR CARRYING OUT REACTIONS IN REACTOR WITH SLOT-SHAPED REACTION SPACES

(75) Inventors: Rüdiger Schütte, Alzenau (DE); Torsten Balduf, Marl (DE); Catrin Becker, Frankfurt (DE); Ina Hemme, Hanau (DE); Birgit Bertsch-Frank, Wuppertal (DE); Werner Wildner, Alzenau (DE); Jürgen Rollmann, Pflaumheim (DE); Georg Markowz, Karlstein (DE)

(73) Assignee: Degussa AG, Essen (DE)

( * ) Notice: Subject to any disclaimer, the term of this patent is extended or adjusted under 35 U.S.C. 154(b) by 528 days.

(21) Appl. No.: 09/934,085

(22) Filed: Aug. 22, 2001

(65) Prior Publication Data

US 2002/0028164 A1    Mar. 7, 2002

(30) Foreign Application Priority Data

Aug. 31, 2000    (DE) ................................. 100 42 746

(51) Int. Cl.
*B01J 19/24*    (2006.01)
*B01J 8/02*    (2006.01)

(52) U.S. Cl. ...................... 422/198; 422/211; 422/222; 422/202; 423/584; 568/476; 562/532; 549/518

(58) Field of Classification Search ................ 422/198, 422/187–191, 193, 196, 197, 200, 211, 220, 422/222; 165/164–167; 366/DIG. 1, DIG. 2, 366/DIG. 3, 341
See application file for complete search history.

(56) References Cited

U.S. PATENT DOCUMENTS 1,662,870 A * 3/1928 Stancliffe ................... 165/166
3,528,783 A * 9/1970 Haselden .................... 422/188
4,153,501 A * 5/1979 Fink et al. ................... 159/49

(Continued)

FOREIGN PATENT DOCUMENTS

DE    33 42 749 A1    5/1984

(Continued)

OTHER PUBLICATIONS

The American Heritage® Dictionary of the English Language, Fourth Edition, (2000). Definition of "slot".*

(Continued)

*Primary Examiner*—Glenn Caldarola
*Assistant Examiner*—Jennifer A. Leung
(74) *Attorney, Agent, or Firm*—Robert G. Weilacher; Smith, Gambrell & Russell

(57) ABSTRACT

Reactions between at least two fluid reactants are performed in a reactor comprising wall elements (1), slot-shaped reaction spaces (3) and cavities (5) for conducting a fluid heat-carrier through. Depending on the process and throughput, a modular structural design is chosen wherein an arbitrary number of wall elements (1) are assembled to a right-parallelepipedal block (24), the reaction spaces (3) are formed between lateral surfaces (2) of right-parallelepipedal wall elements (1), the reactants are introduced into the reaction spaces (3) from edge regions of one side of the block (24) and are conducted through the reaction spaces (3) in parallel flows and the fluid heat-carrier is conducted through the tubular cavities (5) extending in the interior of the wall elements (1).

31 Claims, 9 Drawing Sheets

U.S. PATENT DOCUMENTS

| | | | | |
|---|---|---|---|---|
| 4,820,495 | A | * | 4/1989 | Vu et al. .................... 422/148 |
| 4,973,777 | A | * | 11/1990 | Alagy et al. ................ 585/403 |
| 5,037,619 | A | * | 8/1991 | Alagy et al. ................ 422/191 |
| 5,456,889 | A | * | 10/1995 | Pow et al. .................. 422/173 |
| 5,638,900 | A | * | 6/1997 | Lowenstein et al. ........ 165/168 |
| 5,690,763 | A | * | 11/1997 | Ashmead et al. ............ 156/60 |
| 5,803,600 | A | * | 9/1998 | Schubert et al. ............ 366/144 |
| 5,961,932 | A | | 10/1999 | Ghosh et al. ................ 422/193 |
| 6,132,689 | A | * | 10/2000 | Skala et al. ................. 422/193 |

FOREIGN PATENT DOCUMENTS

| | | |
|---|---|---|
| DE | 44 44 364 C2 | 3/1998 |
| DE | 197 54 185 C1 | 2/1999 |
| DE | 197 48 481 | 5/1999 |
| DE | 198 16 296 A1 | 10/1999 |
| DE | 198 41 302 | 3/2000 |
| EP | 0 691 701 A1 | 1/1996 |
| EP | 0 754 492 A3 | 1/1997 |
| JP | 04310229 A * | 11/1992 |
| JP | 06111838 A * | 4/1994 |
| WO | WO 98 33587 | 8/1998 |

OTHER PUBLICATIONS

PCT Notification of Transmittal of International Search Report (PCT/ISA/220) and PCT International Search Report dated Feb. 20, 2002 (Form PCT/ISA/210).

* cited by examiner

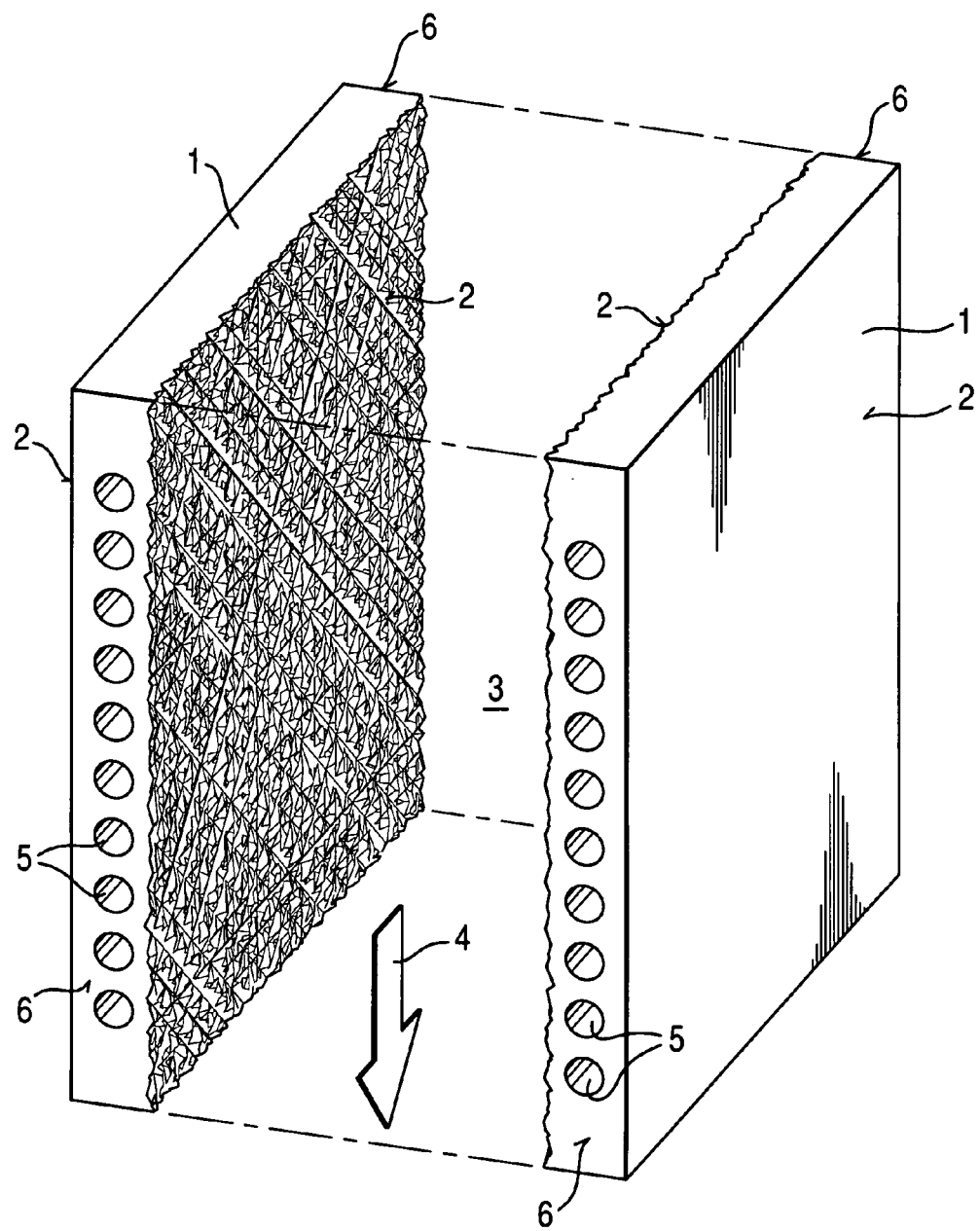

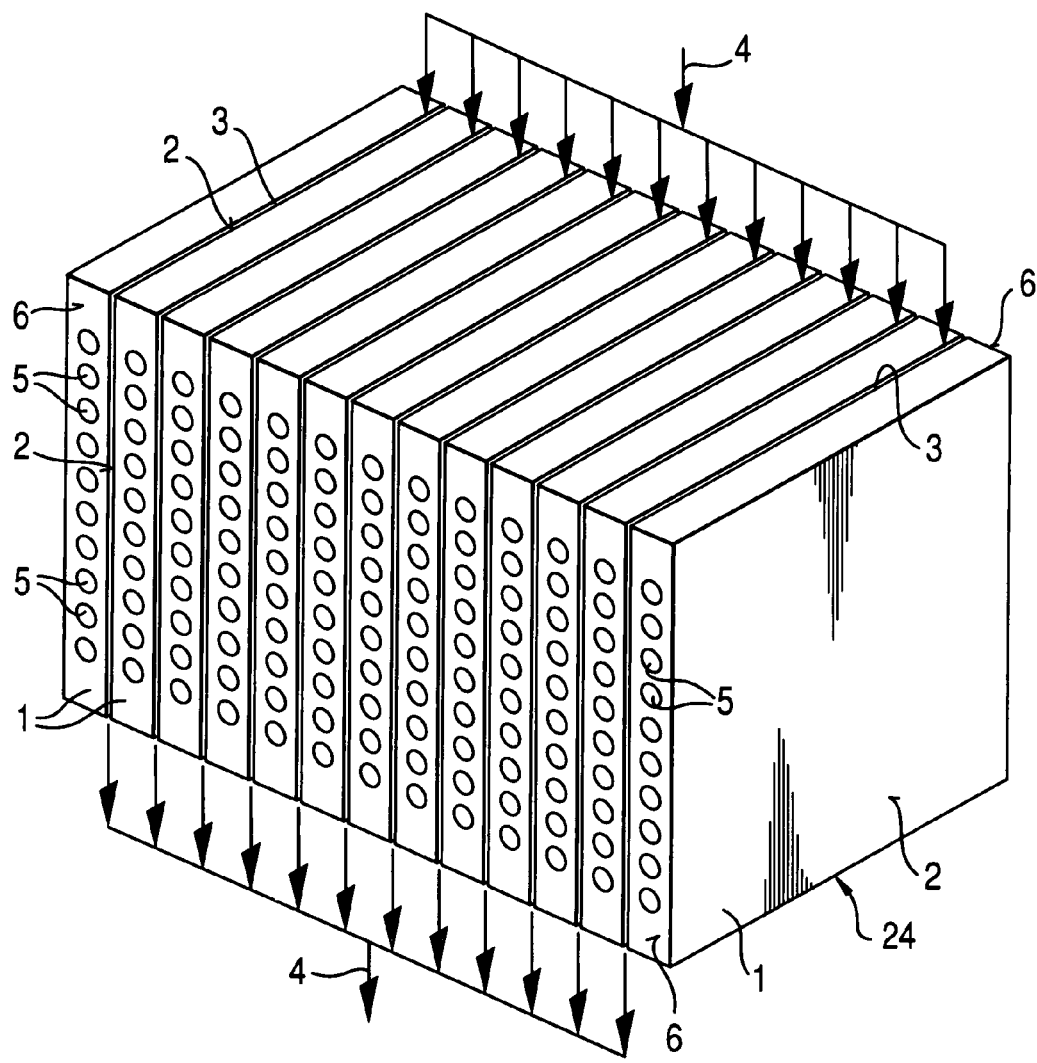

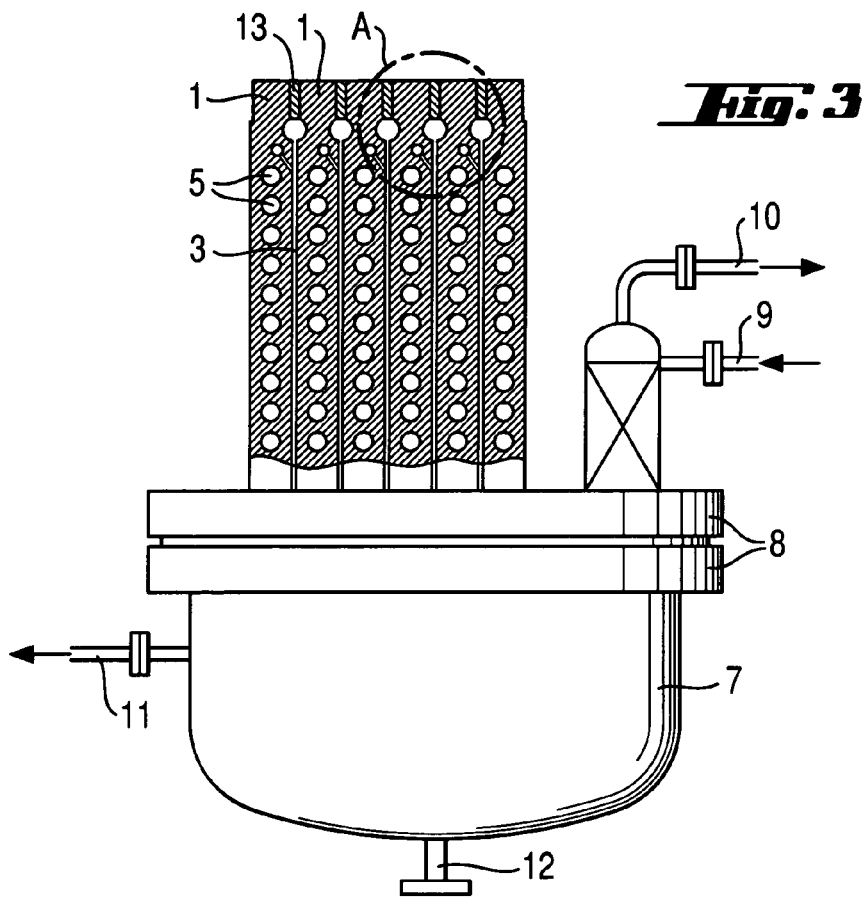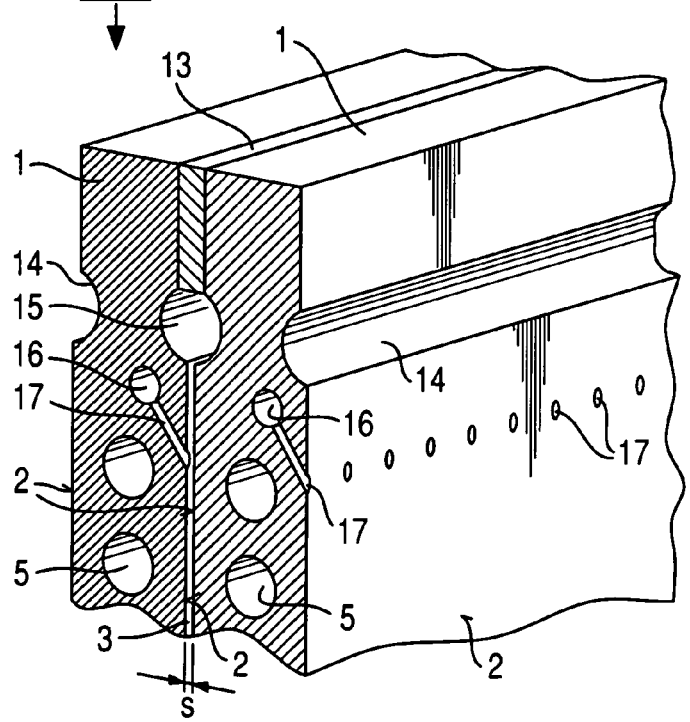

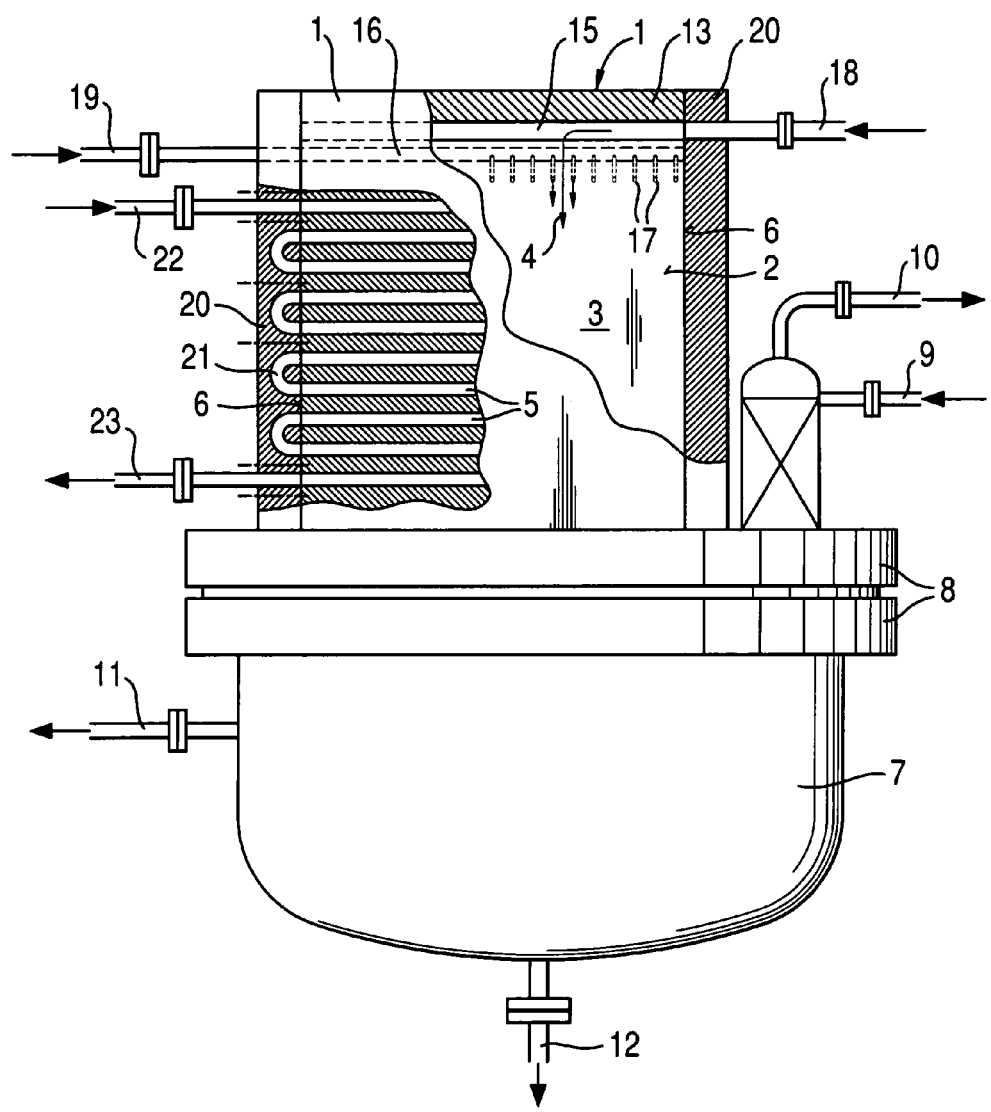

PROCESS AND DEVICE FOR CARRYING OUT REACTIONS IN REACTOR WITH SLOT-SHAPED REACTION SPACES

The present invention relates to a process for carrying out reactions between at least two fluid reactants using a reactor in which there are located wall elements, slot-shaped reaction spaces and cavities for conducting these through a fluid heat-exchange medium.

BACKGROUND OF THE INVENTION

As disclosed in German patent document DE 33 42 749 A1 a plate-type reactor for chemical syntheses under high pressure is known wherein the plates take the form of flat right parallelepipeds which are bounded by sheet-metal walls and which each form a chamber filled with a catalyst, the two largest walls of which are gas-impermeable. Flow of the reaction gases through the granular catalyst takes place either horizontally or vertically through two open or pierced narrow sides of the right parallelepiped which are located opposite each other.

With a view to heating or cooling the reactor (depending on the reaction, either exothermic or endothermic), cooling channels are provided in the chambers for the circulation of a liquid heat-exchange. These cooling channels may be formed by sheet-metal structures which take the form of crosspieces, corrugated sheet metal or such like and which are firmly connected to the smooth walls, for example by welding. The totality of the chambers is adapted in outline to the shape of a cylindrical reactor, so that the chambers have, in part, varying sizes and are perfused in succession by the reaction gases, e.g. also in groups. The structural design is enormously elaborate, and the production output, which as such is already low, can at best be increased by axial lengthening and/or by a parallel connection of several reactors.

EP 0 691 701 A1 disclose a stacked reforming generator wherein, with a view to carrying out endothermic reactions, a reforming chamber with heat-recovery medium connected downstream is embedded in each instance between two combustion chambers. In this case the directions of flow of the gases in the reforming chambers and in the combustion chambers are opposite, semipermeable walls being arranged ahead of the heat-recovery chambers which are connected downstream in each instance. The heat-recovery medium is in the form of spheres of aluminum oxide, for example. With a view to improving the exchange of heat, between the individual chambers there are arranged horizontal heat-conducting sheets which are provided with openings for the passage of fuel in the heating region. Between each such group of three there is located, in turn, a fuel-distributing chamber. The device is extraordinarily complicated in structure and is neither provided nor suitable for exothermic processes since the device possesses no cooling channels, as this would run counter to the sense and purpose of the known art. The structural design, which is not suitable for operation at high pressure, serves the purpose of shortening the overall length by virtue of the omission of special heating zones.

Another development is disclosed in DE 44 44 364 C2; namely, a vertical fixed-bed reactor with rectangular casing cross-section for exothermic reactions between gases, wherein the fixed bed of catalysts is subdivided by vertical partitions for the purpose of forming separate flow channels and a plate-type heat-exchanger. Below and above the flow channels, catalyst-free interspaces are located in each instance in alternating arrangement. The gases emerge at the upper end of the fixed bed from some of the flow channels and are conducted again through lateral overflow channels beneath the fixed bed, from where they are supplied through the respective other flow channels to a gas outlet nozzle. The device is neither provided nor suitable for endothermic processes, since the device possesses no means for a supply of heat. In addition, on account of the rectangular cross-section of the casing the structural design is not suitable for operation at high pressure.

Disclosed in EP 0 754 492 A2 is a plate-type reactor for reactions of fluid media which is constructed in the form of a static mixer with exchange of heat. For this purpose, numerous plates are stacked on top of one another, the lowest of which is closed in the outward direction and the uppermost of which merely possesses bores in the outward direction for the intake and discharge of the media to be caused to react or that have been caused to react and of a heat-exchange medium. The respective second plates from below and from above possess, in addition, recesses which are open on one side for the redirection of the reactants through the stack in a meandering shape. In the plates situated in between there are located X-shaped or cloverleaf-shaped mixing chambers and reaction chambers which are connected to one another in the direction of the stack. The heat-exchanger channel is also guided through the stack of plates in a meandering shape. The plates consist of material with good thermal conductivity, preferably metals and alloys, have a thickness between 0.25 and 25 mm and can be produced by micromachining, etching, stamping, lithographic processes etc. They are firmly and tightly connected to one another on their surfaces outside the apertures, i.e. on the periphery, for example by clamping, bolts, rivets, soldering, adhesive bonding etc., and thereby form a laminate. The complicated flow paths give rise to high resistances to fluid flow and are not capable of being filled with catalysts. On account of the requisite machining, the production process is extremely elaborate, because all the contact surfaces have to be finely ground.

In DE 197 54 185 C1 there is shown a reactor for the catalytic conversion of fluid reaction media wherein a fixed bed consisting of catalyst material which is supported on a sieve plate is subdivided by vertical thermal sheets which each consist of two metal sheets which have been deformed repeatedly in the shape of a cushion and which are welded to one another, including a space for conducting a cooling or heating medium through at points which are distributed in the form of a grid. The reaction media and a heat-exchange medium are conducted in counterflow through the columns of the fixed bed between the thermal sheets, on the one hand, and the cavities in the thermal sheets, on the other hand. The container of the reactor is constructed in the form of a vertical cylinder, and the thermal sheets are adapted to the cylinder, that is to say they have varying sizes. Also in this case the production output can at best be increased by axial lengthening and/or by a parallel connection of several reactors.

DE 198 16 296 A1 from the same applicant shows that it is known to generate an aqueous solution of hydrogen peroxide from water, hydrogen and oxygen in a reactor which may contain both a fixed-bed packing consisting of particulate catalysts and planar monolithic carriers which are provided with channels, take the form of heat-exchangers and are provided with coatings of catalyst material. By way of catalysts, elements from the 8th and/or 1st subgroups of the Periodic Table of Elements are specified, such as Ru, Rh, Pd, Ir, Pt and Au, whereby Pd and Pt are particularly preferred. Activated carbon, water-insoluble oxides, mixed oxides, sulfates, phosphates and silicates of alkaline-earth metals, Al, Si, Sn and of metals pertaining to the 3rd to 6th subgroups are specified by way of carrier materials. Oxides of silicon, of aluminum, of tin, of titanium, of zirconium, of niobium and of tantalum as well as barium sulfate are specified as being preferred. Metallic or ceramic walls having the function of heat-exchangers analogous to plate-type heat-exchangers are named as materials for monolithic carriers. The specified experimental reactor had an inside diameter of 18 mm with a length of 400 mm. The temperatures were within the range from 0 to 90° C., preferably 20 to 70° C., the pressures were between atmospheric pressure and about 10 MPa, preferably between about 0.5 and 5 MPa. Also with respect to this state of the art, the production output can at best be increased by axial lengthening and/or by a parallel connection of several reactors.

The reactors shown in DE 195 44 985 C1 as well as DE 197 53 720 A1 comprise a plate-like heat exchanger wherein the fluid heat-exchange medium is conducted through the slot formed between two plates. There is no hint on the function of width slot-shaped reaction spaces.

Further, there is disclosed a device in DE 197 41 645 A1 which comprises a microreactor with reactions and cooling channels wherein the depth "a" of the reaction channels is<1000 µm and the smallest wall thickness "b" between reaction and cooling channels is<1000 µm. This document gives no indication to use reaction spaces other than said channels. A microreactor comprising many parallel grooves as reaction spaces is taught by DE 197 48 481. The manufacture of a reactor for large scale throughput is expensive.

Furthermore, so-called microreactors are known in which the dimensions of the flow channels are in the region of a few hundred micrometres (as a rule, <100 µm). This results in high transport values (heat-transfer and mass-transfer parameters). The very small channels act as flame barriers, so that no explosions are able to spread. In the case of toxic reactants, a small storage volume (hold-up volume) leads, in addition, to inherently safe reactors. But a filling of the channels with catalysts is impossible by reason of the small dimensions. A further crucial disadvantage is the elaborate production process. In order to avoid clogging of the very small channels, over and above this an appropriate protection of the filter has to be provided for upstream of the reactor. High production outputs can only be obtained by means of parallel connections of many such reactors. Furthermore, the reactors can only be operated at higher pressures when the cooling medium is at the same pressure level.

SUMMARY OF THE INVENTION

An object of the invention is to provide a process and a device with which it is possible to carry out, according as desired, exothermic and endothermic processes whereby several fluid reactants react with each other in the presence or absence of catalysts and whereby the reaction region of the reactor is constructed in a modular design, so that it is possible to adapt the production output to the desired requirements.

The above and other objects of the invention, can be achieved, in the case of the process as described wherein:

a) the slot-shaped reaction spaces are formed between lateral surfaces of, in each instance, two adjacent, substantially equally large and substantially right-parallelepiped wall elements made from solid plates and the wall elements are arranged interchangeably in a block within a virtual right parallelepiped, b) the reactants are introduced into the slot-shaped reaction spaces from edge regions situated on the same side of the block and are conducted through the reaction spaces as reaction mixture in the same directions in parallel flows, and c) the fluid heat-exchange is conducted through the cavities extending in the interior of the wall elements.

BRIEF DESCRIPTION OF THE DRAWINGS

The present invention will be further understood with reference to the accompanying drawings, wherein:

FIG. 1 is a perspective exploded representation of a group consisting of two wall elements, FIG. 2 is a perspective schematic representation of a series arrangement of numerous wall elements according to FIG. 1, FIG. 3 is a vertical sectional view through a series arrangement according to FIG. 2 above the bottom of a pressure-resistant reactor, FIG. 4 is the detail view from circle A in FIG. 3 on an enlarged scale, supplemented in perspective view, FIG. 5 is a partial vertically sectioned side view through the subject of FIG. 3 after rotation about an angle of 90 degrees.

DETAILED DESCRIPTION OF THE INVENTION

Figure 6:
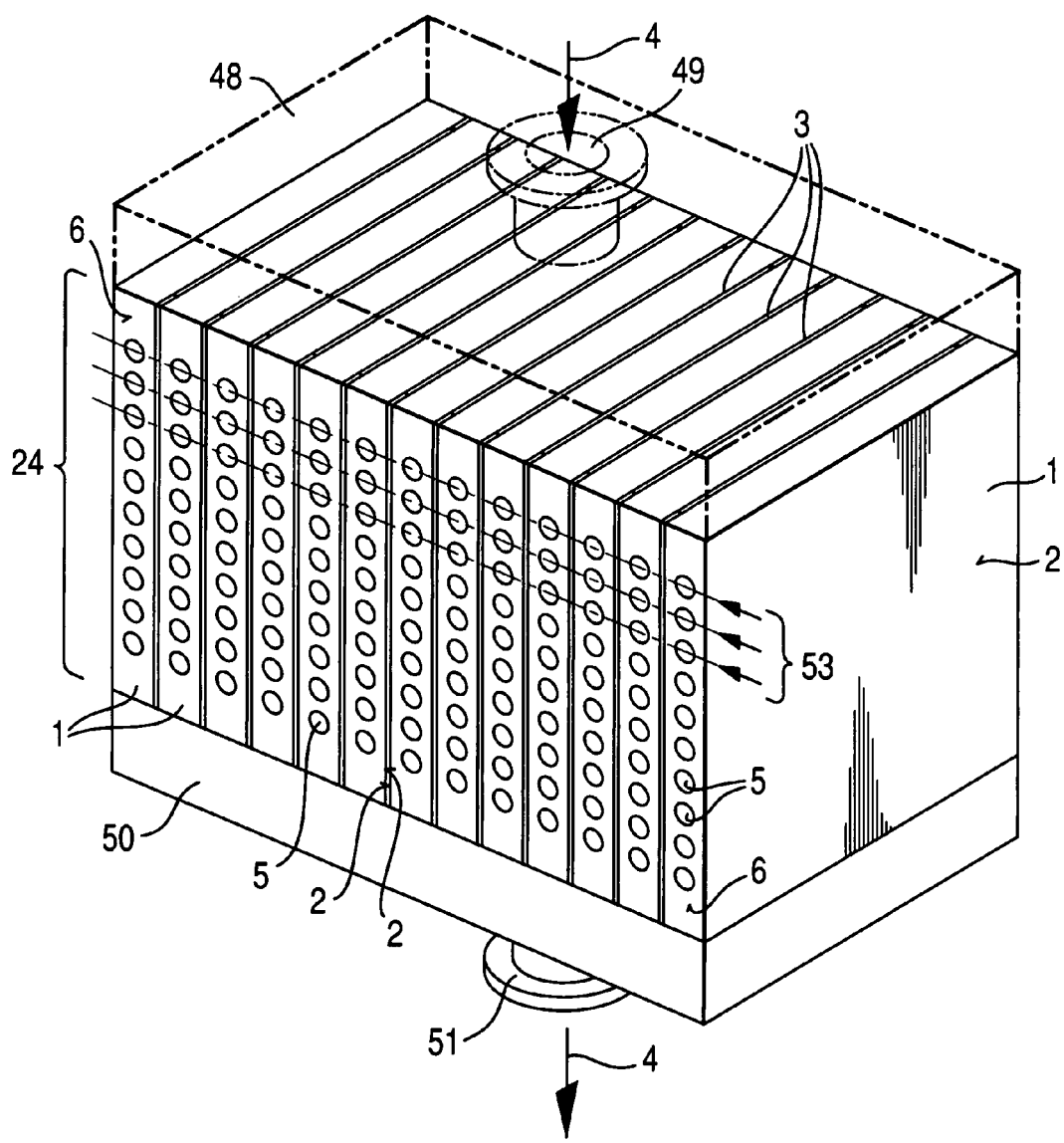
FIG. 6 is the subject of FIG. 2, schematically supplemented by a distributing space and a collecting space for educt(s) and product.

In accordance with the present invention it is possible to achieve the object as described above; and in particular, it is possible to carry out, as desired, exothermic and endothermic processes whereby several fluid reactants (gases and/or liquids) react with each other in the presence or absence catalysts and whereby the reaction region of the reactor is constructed in a modular design, so that it is possible to adapt the production output to the intended requirements. By reducing width of the reaction spaces from e.g. 5 mm to 0.05 mm the ratio of the surface to the volume of the reaction spaces increases. As a result, problems arising from the limited heat transfer within gases are decreased, so that highly exothermic or endothermic reactions can be performed safely.

However, still further advantages can be achieved in accordance with the present invention:

combination of microreaction technology with the advantages of simple manufacture according to classical workshop techniques, easy interchange of individual wall elements (the term "substantially equally large and substantially right-parallelepiped" means that minor deviations, caused by construction reasons, are tolerable), virtually any desired thickness of the wall elements without impairment of function, enlargement of the specific surface area by profiling/roughening, direct total or partial coating of the lateral surfaces with varying catalyst material by impregnating, spraying, printing or such like with varying thickness, filling of the reaction spaces with catalyst particles of varying size, possibilities of gas/gas reactions, gas/liquid reactions, liquid/liquid reactions, impression of flow patterns and flow channels, e.g. for drainage and for allowing liquid reaction products to flow off, simple separation, possibility of altering the slot widths, mixing of the reactants only in the reaction spaces, good reaction control, avoidance of backflows out of the reaction spaces, good controllability by reason of high heat-transfer coefficients and large surfaces, i.e. rapid response to changes in loading and/or in the desired temperature values and uniform temperature profile and thereby longer service lives of the catalyst by avoidance of "hot spots", inherent safety in the course of causing otherwise explosive reaction mixtures to react, small dead volume ("hold-up volume"), possibility of working under high pressure, slight losses of pressure in the reaction spaces, immersibility in liquid solvents and operability with a sump which can be temperature-controlled (heated/cooled) from outside and which enables a gentle termination of the reaction by "quenching" and/or washing, possible addition of inhibitors in order to prevent secondary reactions, reducibility of the volume of the gas/liquid by means of filling materials and/or displacers in the pressure vessel on the other side of the product outlet in the sump, reduction in the number of connections and easier sealability as regards leakages (important in the case of toxic components), low resistances to diffusion, high space-time yields, in particular higher throughputs than in the case of the known microreactors, simpler "scale-up" from the laboratory scale to the production scale by multiplication ("number-up"), simple and compact structural design, reduction of investment costs and operating costs (maintenance, consumption of energy), possibility of the construction of small plants.

In this connection it is particularly advantageous, within the scope of further configurations of the process according to the invention, if—either individually or in combination the following conditions are observed:

at least one reactant is supplied through the wall elements and is introduced into the reaction space in question through at least one of the lateral surfaces of the wall elements, a distributing medium, from which the reaction spaces are provided with the reactants, is arranged on at least one side of the block, by way of distributing medium, use is made of a solid body with groups of channels, the cross-sections of which are chosen to be sufficiently small to avoid spreading of flames in them in the course of the supply of reactants that form an explosive mixture, by way of distributing medium, use is made of a packing material with a particle size and with interspaces that are chosen to be sufficiently small to avoid spreading of flames in them in the course of the supply of reactants that form an explosive mixture, the slot width of the reaction spaces is preferably chosen between 0.05 and 5 mm and more preferred 0.05 to 0.2 mm, in case of explosive reactions mixtures the slot width is chosen sufficiently small to avoid spreading of flames, the reaction spaces are filled with granular catalyst, the lateral surfaces of the wall elements facing towards the reaction spaces are at least partially coated with catalyst material, the lateral surfaces of the wall elements facing towards the reaction spaces are provided with a profiled structure for the purpose of enlarging the surface area, the wall elements are immersed at least partially in an aqueous or organic solvent or solvent mixture, by way of solvent, use is made of water, optionally with at least an addition of inhibitors that prevent a decomposition and/or degradation of the reaction product, and/or, if the process is used for the purpose of producing hydrogen peroxide from water (vapour), hydrogen and air, optionally enriched with oxygen, or oxygen.

The invention also relates to a device for carrying out reactions between at least two fluid reactants using a reactor in which there are located a plurality of wall elements, a plurality of slot-shaped reaction spaces and a plurality of cavities through which a fluid heat-exchange medium is conducted.

With a view to achieving the same object, such a device is characterised, according to the invention, in that a) the slot-shaped reaction spaces are arranged between lateral surfaces of, in each instance, two adjacent, substantially equally large and substantially right-parallelepipedal wall elements made from solid plates and in that the wall elements are arranged interchangeably in a block within a virtual right parallelepiped, b) the supply of the reactants into the slot-shaped reaction spaces is capable of being carried out from the same side of the block, the reaction mixture being capable of being guided through the reaction spaces in the same directions and in parallel flows and in that c) the wall elements contain tubular cavities for conducting the fluid heat-exchange medium through the wall element.

The process and the device are suitable, in exemplary manner, for the following processes:

selective hydrogenations and oxidations, production of acrolein by catalytic oxidation of propene with an $O_2$-containing gas having elevated oxygen concentration in comparison with air, accompanied by an increase in selectivity, for example in the presence of a Mo-containing catalyst at a temperature within the range from 350 to 500° C. and at a pressure within the range from 0.1 to 5 MPa, production of acrylic acid by catalytic oxidation of propene, for example in the presence of a Mo-containing catalyst and a promoter at 250 to 350° C. and at 0.1 to 0.5 MPa, production of ethylene oxide or propylene oxide from ethylene or propylene, respectively, and gaseous hydrogen peroxide in the presence of an oxidic or siliceous catalyst, such as titanium silicalite, at a temperature within the range from 60 to 200° C. and at a pressure within the range from 0.1 to 0.5 MPa, direct synthesis of hydrogen peroxide from $H_2$ and $O_2$ or an $O_2$-containing gas in the presence of a noble-metal catalyst and water or water vapour—for example according to the process disclosed in DE-A 198 16 296 and according to those processes disclosed in further documents cited therein. By way of catalysts in this connection, use can be made of elements from the 8th and/or 1st subgroups of the Periodic Table of Elements, such as Ru, Rh, Pd, Ir, Pt and Au, whereby Pd and Pt are particularly preferred. The catalysts may be employed per se, e.g. as suspension catalysts, or in the form of supported catalysts by way of packing in the slot-shaped reaction spaces, or they are fixed to the wall elements, directly or through layer-forming supporting materials. By way of supporting materials, use can be made of activated carbon, water-insoluble oxides, mixed oxides, sulfates, phosphates and silicates of alkaline-earth metals, Al, Si, Sn and of metals belonging to the 3rd to 6th subgroups of the Periodic Table of Elements. Oxides of silicon, of aluminum, of tin, of titanium, of zirconium, of niobium and of tantalum as well as barium sulfate are preferred. In the case of the direct synthesis of hydrogen peroxide, the reaction temperatures lie, for example, within the range from 0 to 90° C., preferably 20 to 70° C., the pressures lie between atmospheric pressure and about 10 MPa, preferably from about 0.5 and 5 MPa.

In this connection it is particularly advantageous, within the scope of further configurations of the device according to the invention, if—either individually or in combination the following structural parameters are observed:

in the wall elements there is arranged, in each instance, at least one feed channel which leads into the reaction space in question through at least one of the lateral surfaces of the wall elements, on at least one side of the block there is arranged a distributing medium through which the reaction spaces are capable of being provided with the reactants, the distributing medium is a solid body with groups of channels, the cross-sections of which are chosen to be sufficiently small to avoid spreading of flames in them in the course of the supply of reactants that form an explosive mixture, the distributing medium is a packing material with a particle size and with interspaces that are chosen to be sufficiently small to avoid spreading of flames in them in the course of the supply of reactants that form an explosive mixture, the slot width of the reaction spaces preferably amounts to between 0.05 and 5 mm and especially preferred to 0.05 to 0.2 mm, the reaction spaces are filled with granular catalyst, the lateral surfaces of the wall elements facing towards the reaction spaces are at least partially coated with catalyst material, the lateral surfaces of the wall elements facing towards the reaction spaces are provided with a profiled structure for the purpose of enlarging the surface area, the wall elements are partially or completely arranged in a closed vessel, the reaction spaces on the narrow sides of the wall elements extending parallel to the direction of flow of the reactants are closed by plates in which there are located openings for the feeding and drainage of a heat-exchange medium into the wall elements and out of the wall elements, in the plates there are located further openings for the feeding of at least one of the reactants into the wall elements and the wall elements are each provided with at least one feed channel which via discharge openings leads, in each instance, into one of the reaction spaces, the wall elements are each provided with a group of tubular cavities which extend parallel to the lateral surfaces of the wall elements and are closed at their ends by the plates which are mounted onto the narrow sides of the wall elements and in which openings for the heat-exchange medium that are in alignment with the cavities are located, the plates are provided on their outsides and ahead of the openings with flow channels extending at right angles to the wall elements for at least one of the reactants and/or a heat-exchange medium, the plates are covered on their outsides facing away from the wall elements by a distributing body in which there are located flow channels into which the openings in the plates lead, the wall elements are formed by two subelements having semicylindrical or otherwise shaped recesses whereby tubular cavities are formed by two respective subelements pressing together, at least two, preferably 5 to 50 wall elements are accommodated as a block in a pressure vessel, the pressure vessel is capable of being filled at least partially with a solvent, the pressure vessel possesses a lid with a partition wall and two connecting ports for the feeding of two reactants and the partition wall is capable of being mounted onto the distributing medium, the slot width of the reaction spaces is capable of being changed by varying the thickness of spacers.

Exemplary embodiments of the subject-matter of the invention will be elucidated in greater detail below on the basis of FIGS. 1 to 10.

In FIG. 1 there are shown-in exploded representation-two wall elements 1 with lateral surfaces 2 which include between themselves a reaction space 3 through which the reactants flow in the direction of the arrow 4. In each of the wall elements there are arranged cavities 5 in the form of through bores or channels which extend parallel to the lateral surfaces 2 and terminate in the narrow sides 6 of the wall elements 1. Alternative embodiments are specified further below.

The wall elements 1 take the form of flat right parallel-epipeds, the largest surfaces of which are the lateral surfaces 2. These lateral surfaces 2 may-as is shown-be provided with a profiled structure, that is to say they may be roughened, for example, in order to enlarge the effective surface area. The lateral surfaces 2 may furthermore be wholly or partially provided with surface deposits including a catalyst material, but this is not shown separately here. Further particulars are evident from FIG. 4. It is also possible, alternatively or in addition, to arrange particulate catalysts in the reaction space 3, the size of which is adapted to the slot width "s" (FIG. 4).

FIG. 2 shows the combination of thirteen such equally large wall elements I so as to form a right-parallelepipedal block 24; however, this number is variable, and therein lies one of the essential purposes of the invention, namely, the possibility of adaptation to varying production outputs and processes. The mass transport in unidirectional parallel flows—here shown from above in a downward direction—is suggested by means of arrows.

FIG. 3 shows a vertical section through a series arrangement according to FIG. 2 above the bottom 7 of a pressure-resistant reactor, the lower flanged joint 8 of which is shown here. The supply of liquid solvents is effected via the pipe 9, the removal of residual gases is effected via the pipe 10, the removal of the end product is effected via the pipe 11, and the removal of sump material is effected via the pipe 12, optionally with a view to cleaning.

FIG. 4 shows the detail from circle A in FIG. 3 on an enlarged scale and supplemented in perspective view, i.e. the circumstances on both sides of a reaction space 3. The slot width "s" of the reaction space 3 is maintained at a predetermined measurement by spacers 13 and is chosen, for example, between 0.05 and 5 mm. However, this range may also be decreased or exceeded. In case of highly exothermic and endothermic reactions, especially comprising an explosive gas mixture, the slot width is reduced until any flame spreading is avoided. The optimal lot width depends on the reaction medium and reaction type and is determined by experiments. As can be seen from FIGS. 4 and 6 the slot width "s" of the inventive device is significantly smaller than the thickness of the wall elements. In the tubular wall elements there are located the cavities or channels 5, which have already been described, for conducting a fluid heat-exchange medium through. Depending on the temperature control thereof, heat can be dissipated in the case of an exothermic process or heat can be supplied in the case of an endothermic process. By way of heat-exchange medium, use can be made of water, oils, gases and optionally also the product itself.

In the wall elements 1 there are located furthermore semicylindrical recesses 14 which complement one another so as to form a substantially cylindrical feed channel 15 for a first reactant. In addition, located in the wall elements are further feed channels 16 for at least one further reactant. The feed channels 16 are connected to the respective reaction space 3 by means of discharge openings 17, whereby the discharge openings 17 lead into the lateral surfaces 2 of the wall elements so that the reactants are able to mix in the reaction spaces 3. The cavities 5, the feed channels 15 and 16 and also the row(s) of discharge openings 17 are parallel to one another and to the lateral surfaces 2 of the wall elements 1 and extend over the entire length thereof, as viewed in the horizontal direction.

The cooling channels (=tubular cavities 5) may, in a manner analogous to the formation of the feed channels 15 according to FIG. 4, also be configured in such a way that each wall element 1 is split parallel to the lateral surfaces 2 into two subelements and semicylindrical or otherwise shaped recesses are arranged in the slot surfaces. As a result of pressing the respective two corresponding subelements together, cavities 5 are formed, through which a fluid heat-exchange medium is able to flow. The term "tubular" is intended to encompass round or square-formed channels or pipes.

The slot width "s" is so chosen that no flames are able to spread in the reaction spaces 3 in the case of explosive reaction mixtures. In special cases, the local formation of explosions in the reaction spaces may also be permitted, in which case care has only to be taken structurally to ensure that these explosions do not flash over to adjacent reaction spaces.

Important in this connection is the fact that the feed channels 15 and 16 extend in the (upper) edge region of the wall elements 1 or of the reaction spaces 3, so that virtually the entire (vertical) length of the reaction spaces 3 is available for the reaction. Further particulars of and alternatives to the supply and removal of reactants and heat-exchange medium will be elucidated in still more detail on the basis of the following.

FIG. 5 shows a partially sectioned side view through the subject of FIG. 3 after rotation about a vertical axis by an angle of 90 degrees. Two reactants are supplied to the system through the feed pipes 18 and 19: in the case of the production of hydrogen peroxide, air via feed pipe 18 and hydrogen via feed pipe 19. The transport of the fluid heat-exchange medium through the cavities 5 will also be elucidated in greater detail on the basis of FIG. 5, i.e., the narrow sides 6 of the wall elements 1 are closed by mounted plates 20 in which there are arranged U-shaped channels 21 for the connection of, in each instance, two cavities 5. However, this is only represented on the left-hand side of the block. The heat-exchange medium is supplied through a feed pipe 22 and is removed through a drain 23.

For the wall elements, use may be made of sufficiently heat conductive, preferable metallic, substantially right-parallelepipedal plates. The wall elements 1, which are preferably made out of metal (e.g. stainless steel), may consist of solid plates with appropriate bores (cavities 5 and feed channels 16) and recesses 14. Alternatively, the cavities 5 may be combined, optionally also in groups, in which case conducting devices, e.g. ribs, for guidance of the heat-exchange medium are arranged within the cavities which are then larger. The wall elements 1 may also be composed of two plate-like subelements which are connected to one another in sealed manner, for example screwed together. The only important point is that they withstand the considerable pressure differences, which in some cases can be significant, (up to 10 MPa or 100 bar) between the heat-exchange medium and the reactants.

FIG. 6 shows the subject of FIG. 2, schematically and complemented in thick lines by an upper distributing space 48 with a central feed pipe 49 for educt(s) and a lower collecting space 50 with a drain 51 for the product. One of the reactants or a mixture of the reactants R1 and R2 can be supplied via the distributing space 48. In the case of a mixture, the feed pipes 15 and 16 (in FIG. 4) can be dispensed with if the spacers 13 are interrupted. In the case of explosive reaction mixtures, in addition to the procedure according to the arrangement in FIG. 2 a procedure according to the arrangements in FIGS. 8 to 10 can also be adopted.

Figure 7:
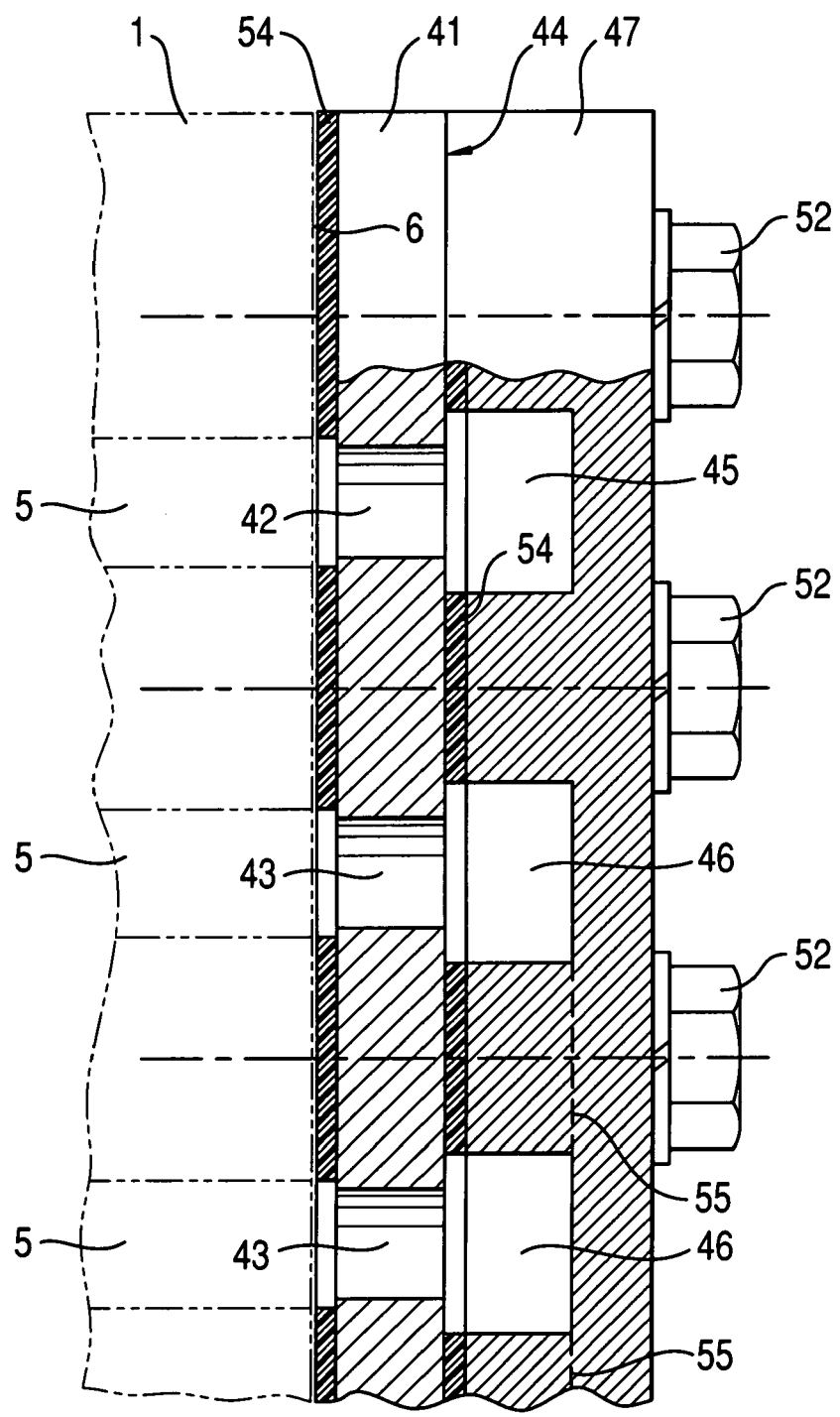
FIG. 7 is a vertical sectional view through a plate and a distributing body with flow channels for reactants and/or heat-exchange medium.

The open narrow sides 6 of the wall elements 1 can be covered by a plate combination, consisting of a plate 41 and a distributing body 47, which is designed to be uninterrupted over the width and height of all the wall elements 1 and which is represented, on a greatly enlarged scale, in FIG. 7. FIG. 7 shows a vertical section through the upper edge region of such a plate combination 41/47 with a flow channel 45 for one of the reactants and with flow channels 46 for the heat-exchange medium. For the intake and/or discharge thereof, openings 42 and 43 which are connected to the flow channels 45 and 46 in the distributing body 47 are arranged in the plate 41.

The flow channels 45 and 46, which extend perpendicular to the plane of the drawing, are formed, for example, by grooves in the distributing body 47. The grooves may be produced by metal-cutting, by casting or forging. This results in great stability of form which withstands the pressure differences that are demanded. This plate combination 41/47, with its openings 42 and 43 in alignment with the associated channels in the wall elements 1, is now screwed in sealing manner by means of a gasket 54 onto all the narrow sides 6 of the wall elements 1 of the block 24. Only a few of the numerous screw joints 52 are represented. By this means, a provision of the wall elements 1 is effected corresponding to the arrows 53 in FIG. 6. By means of dashed lines 55 it is indicated that several flow channels 46 may also be combined to form a common flow channel or distributing space.

The plate combination 41/47 may also be redesigned to the effect that it is suitable for a provision of wall elements 1 according to FIG. 4.

Figure 8:
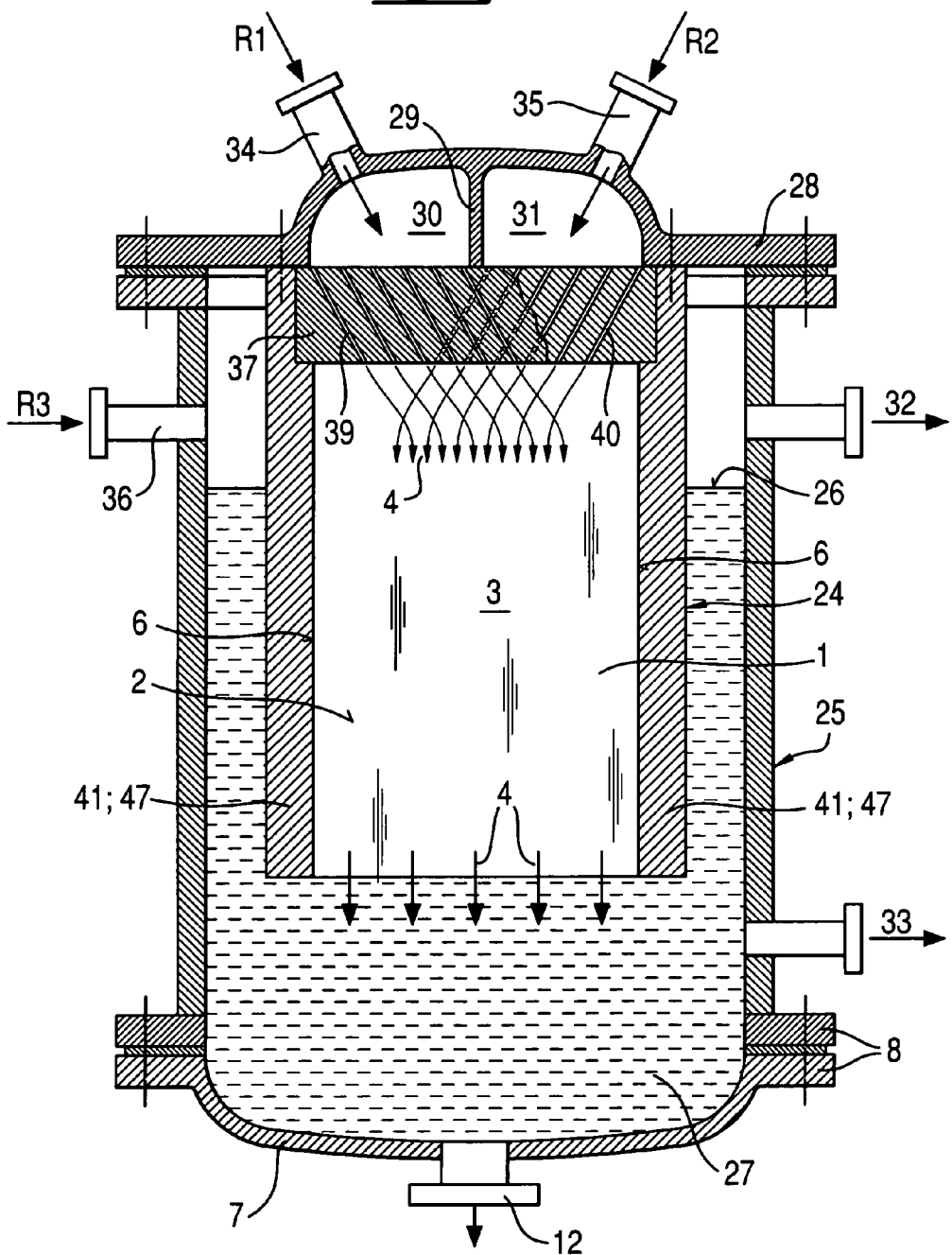
FIG. 8 is a partial vertical sectional view through a first exemplary embodiment of a reactor with a pressure vessel.

FIG. 8 shows, on the basis of a partial vertical section, a schematic representation of a complete reactor, e.g. for the production of hydrogen peroxide. A right-parallelepipedal block 24 consisting of several wall elements I according to FIGS. 1 and 2 is suspended from above in a pressure vessel 25 which is filled with a solvent 27, for example water, to a level 26. The slot-shaped reaction spaces 3 extend parallel to the plane of the drawing.

At the top the pressure vessel 25 possesses a lid 28 which is subdivided by a partition 29 into two chambers 30 and 31, the partition 29 being mounted in sealing manner onto a distributing medium 37 which consists of a solid body (preferably made of metal) with two separate groups of narrow channels 39 and 40. The channels 39 extend in the solid body from the chamber 30 to the upper ends of the reaction spaces 3, the channels 40 extend from the chamber 31 to the upper ends of the reaction spaces 3. In these channels 39 and 40 the reactants are accordingly unable to mix, but, even if this were to happen, no flames are able to spread in the channels 39 and 40. Mixing of the reactants takes place only in the reaction spaces 3, in which likewise no flames are able to spread if it is a question of a reaction mixture that is explosive as such. The explosive properties of the reaction mixture are material-dependent and reaction-dependent and have to be determined in the given case.

Through a connecting port 34 a first reactant "R1" is supplied to chamber 30, and through a further connecting port 35 a second reactant "R2" is supplied to chamber 31. The waste gases that are not needed are conducted away according to arrow 32, the product is withdrawn according to arrow 33, and the sump can be emptied through the pipe 12. FIG. 8 shows, in addition, another connecting port 36 for a third reactant "R3" and/or a solvent such as water. The plates 41 which are applied at both ends are only indicated very schematically.

Figure 9:
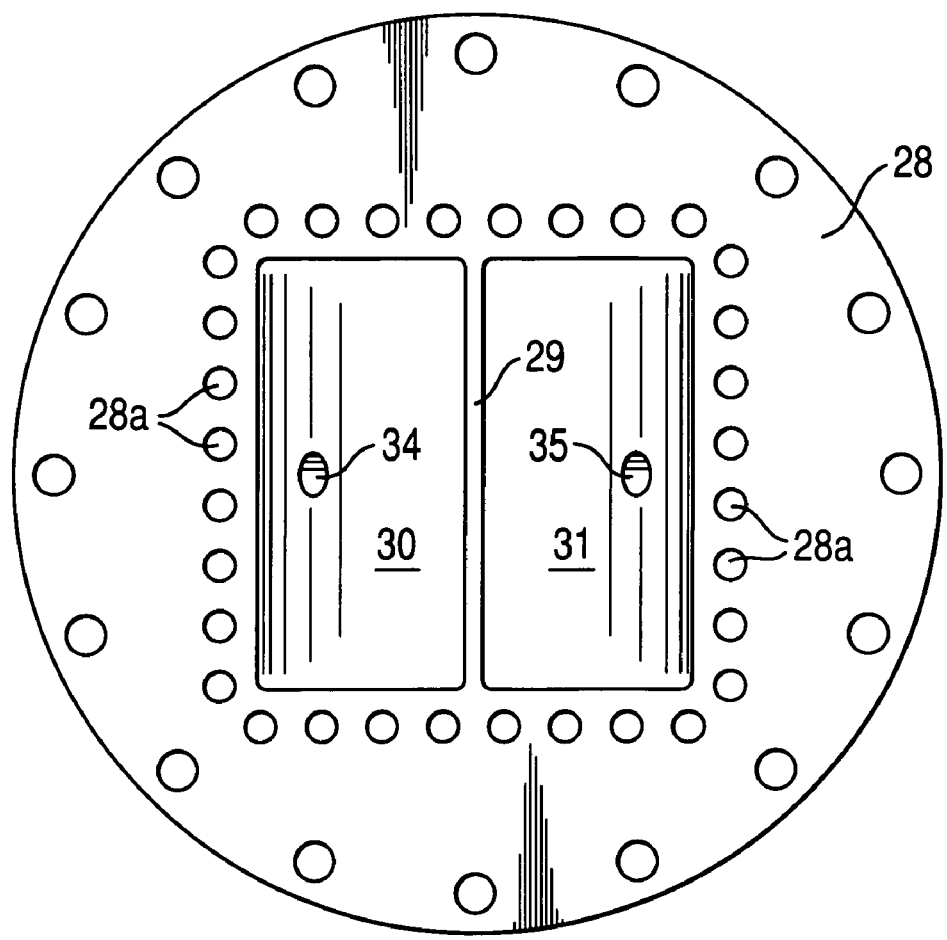
FIG. 9 is a bottom view of the lid of the pressure vessel according to FIG. 8.

FIG. 9 shows a bottom view of the lid 28 of the pressure vessel 25 according to FIG. 8. Bores 28*a* serve for screw coupling.

Figure 10:
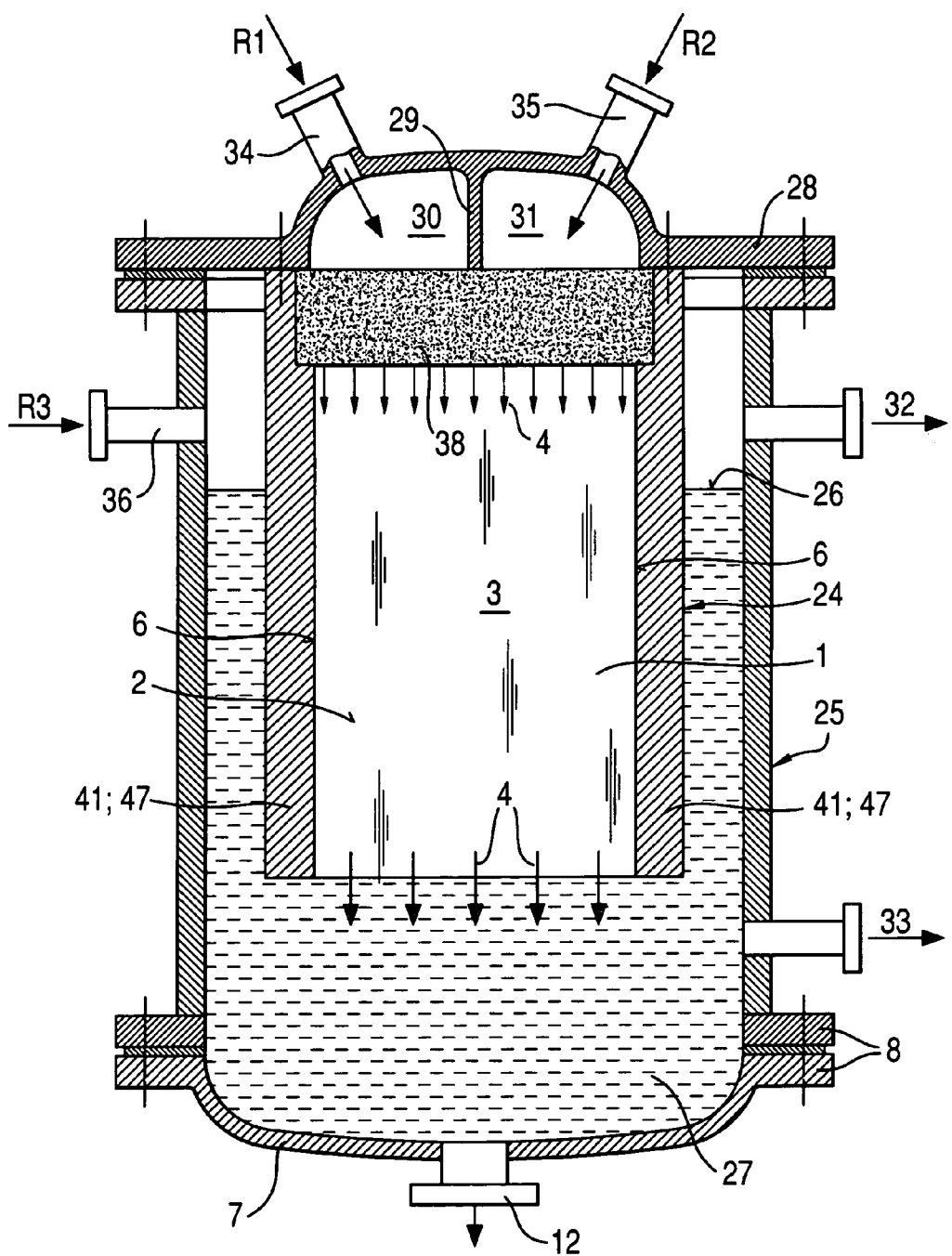
FIG. 10 is a partial vertical sectional view through a second exemplary embodiment of a reactor with a pressure vessel.

FIG. 10 differs from FIG. 8 in that, by way of distributing medium 38, there is arranged above the block 24 of wall elements 1 a packing material which consists of heat-conducting particles, for example sand, grit, metal shavings, metallic fibres or such like, which rest on a sieve plate which is not shown. In this distributing medium 38 the reactants R1 and R2 already mix in accordance with random distribution before they enter the reaction spaces 3. However, the distributing medium forms such narrow interspaces that, likewise, no spreading of flames with explosive consequences is able to occur in them.

The spatial location of the wall elements 1 is essentially a matter of choice: in accordance with the Figures, they may be arranged in a horizontal series arrangement, but they may also be arranged in a vertical stack. The direction of the parallel flows can also be adapted to practical needs: as shown, the parallel flows can be guided vertically from the top downwards, but they may also be guided the other way round, from the bottom upwards. The parallel flows may also run horizontally. As a result, the block 24 with the plates 41 and the connections can be "rotated" into various spatial locations.

Further variations and modifications of the foregoing will be apparent to those skilled in the art and are intended to be encompassed by the claims appended hereto.

German priority application 100 42 746.4 of Aug. 31, 2000 is relied on and incorporated herein by reference.

We claim:

1. A process for carrying out a reaction between at least two fluid reactants in a reactor having a plurality of wall elements, each of the wall elements comprising a plurality of tubular cavities being parallel to each other for conducting a fluid heat-exchange medium there through and a plurality of slot-shaped reaction spaces,
    a) each of said slot-shaped reaction spaces is formed by the lateral surfaces of two spaced apart, substantially equally large and substantially right-parallelepipedal wall elements made of solid plates and wherein the wall elements are arranged interchangeably in a block within a virtual right parallelepiped, comprising
    b) introducing the reactants into the slot-shaped reaction spaces from edge regions situated on the same side of the block and conducting said reactants through the reaction spaces as a reaction mixture in the same directions in parallel flows,
    c) conducting the fluid heat-exchange medium through the tubular cavities, extending in the interior of the wall elements to thereby obtain a desired reaction, and
    d) supplying at least one reactant through the wall elements and into the reaction space through at least one of the lateral surfaces of the wall elements, wherein the slot-shaped reaction spaces have a slot width of between 0.05 and 5 mm, whereby in case of explosive reaction mixtures the slot width of the slot-shaped reaction spaces is chosen sufficiently small in order to avoid spreading of flames.

2. The process according to claim 1, wherein said reactants are introduced into the reaction spaces by a distributing medium on at least one side of the block.

3. The process according to claim 2, further comprising supplying the reactants by said distributing medium which is made of a solid body with groups of channels, the cross-sections of which are chosen to be so small that no spreading of flames is possible in them in the course of the supply of reactants that form an explosive mixture.

4. The process according to claim 2, further comprising supplying the reactants by said distributing medium which is made of a packing material with a particle size and with interspaces that are chosen to be so small that no spreading of flames is possible in them in the course of the supply of reactants that form an explosive mixture.

5. The process according to claim 1, further comprising filling the reaction spaces with granular catalyst before the reaction is carried out.

6. The process according to claim 1, further comprising before carrying out said reaction at least partially coating the lateral surfaces of the wall elements facing towards the reaction spaces with catalyst material.

7. The process according to claim 1, further comprising before carrying out said reaction enlarging the surface area of the lateral surfaces of the wall elements facing towards the reaction spaces by forming a profiled structure on said surfaces.

8. The process according to claim 1, further comprising immersing the wall elements at least partially in a solvent.

9. The process according to claim 8, wherein water is the solvent.

10. The process according to claim 8, further comprising adding at least one stabilizing additive for countering decomposition or degradation of the reaction product to the solvent.

11. The process according to claim 1 wherein said reaction is the direct synthesis of hydrogen peroxide from hydrogen and oxygen or an $O_2$-containing gas in the presence of a catalyst containing at least one element from the 8th and/or 1st subgroups of the Periodic Table of Elements and water or water vapour.

12. The process according to claim 1 wherein said reaction is for the production of propenal from propene and an $O_2$-containing gas in the presence of a catalyst.

13. The process according to claim 1 wherein said reaction is for the production of acrylic acid from propene and an $O_2$-containing gas in the presence of a catalyst and a promoter.

14. The process according to claim 1 wherein said reaction is for the production of ethylene oxide or propylene oxide from ethylene or propylene, respectively, and gaseous hydrogen peroxide in the presence of an oxidic or siliceous catalyst.

15. An apparatus for carrying out a reaction between at least two fluid reactants comprising a reactor in which there are located a plurality of wall elements, and a plurality of slot-shaped reaction spaces, wherein,
   a) each of said slot-shaped reaction spaces is formed by the lateral surfaces of two spaced apart, substantially equally large and substantially right-parallelepipedal wall elements made of solid plates and the wall elements being arranged interchangeably in a block within a virtual right parallelepiped,
   b) the slot-shaped reaction spaces are able to have the reactants supplied from the same side of the block, and are oriented to guide the reaction mixture through the reaction spaces in the same directions and in parallel flows,
   c) the slot-shaped reaction spaces have a slot width of between 0.05 and 5 mm, whereby in case of explosive reaction mixtures the slot width of the slot-shaped reaction spaces is chosen sufficiently small in order to avoid spreading of flames;
   d) each wall element comprises a plurality of tubular cavities being parallel to each other for conducting a fluid heat-exchange medium there through, and
   e) each wall element comprises at least one feed channel for at least one reactant, which feed channel leads into the reaction space through at least one of the lateral surfaces of the wall element.

16. The apparatus according to claim 15, further comprising a distributing medium on at least one side of the block through which the reaction spaces are capable of being provided with the reactants.

17. The apparatus according to claim 16, the distributing medium is a solid body with a plurality of channels, the cross-sections of which are chosen to be sufficiently small to avoid spreading of flames in them in the course of the supply of reactants that form an explosive mixture.

18. The apparatus according to claim 16, the distributing medium is a packing material with a particle size and with interspaces that are chosen to be sufficiently small to avoid spreading of flames in them in the course of the supply of reactants that form an explosive mixture.

19. The apparatus according to claim 15, wherein the reaction spaces are filled with granular catalyst.

20. The apparatus according to claim 15, wherein the lateral surfaces of the wall elements facing towards the reaction spaces are at least partially coated with catalyst material.

21. The apparatus according to claim 15, further comprising the lateral surfaces of the wall elements facing towards the reaction spaces being provided with a profiled structure for the purpose of enlarging the surface area.

22. The apparatus according to claim 15, further comprising the reaction spaces are covered on the narrow sides of the wall elements extending parallel to the direction of flow of the reactants by plates in which there are located openings for the feeding and drainage of a heat-carrier into the wall elements and out of the wall elements.

23. The apparatus according to claim 22, further comprising in said plates there are located further openings for feeding at least one of the reactants into the wall elements and the wall elements are each provided with at least one feed channel which leads via a discharge opening into one of the reaction spaces.

24. The apparatus according to claim 22, further comprising said wall elements are each provided with a group of cavities which extend parallel to the lateral surfaces of the wall elements and are closed at their ends by the plates which are mounted onto the narrow sides of the wall elements and in which the openings for the heat-exchange medium which are in alignment with the cavities are located.

25. The apparatus according to claim 22, further comprising the plates are provided on their outsides and ahead of the openings with flow channels extending at right angles to the wall elements for at least one of the reactants and/or the heat-carrier.

26. The apparatus according to claim 23, further comprising the plates are provided on their outsides and ahead of the openings with flow channels extending at right angles to the wall elements for at least one of the reactants and/or the heat-carrier.

27. The apparatus according to claim 25, further comprising the plates are covered on their outsides facing away from the wall elements by a distributing body in which the flow channels are located into which the openings in the plates lead.

28. The apparatus according to claim 26, further comprising the plates are covered on their outsides facing away from the wall elements by a distributing body in which the flow channels are located into which the openings in the plates lead.

29. The apparatus according to claim 15, wherein the wall elements are accommodated as a block in a pressure vessel.

30. The apparatus according to claim 16, wherein the wall elements are accommodated as a block in a pressure vessel and the pressure vessel possesses a lid with a partition and two connecting sockets for the feeding of two reactants, said partition being capable of being mounted onto the distributing medium.

31. The apparatus according to claim 15,
   wherein the slot width ("s") of the reaction spaces can be changed by varying the thickness of spacers.

* * * * *